United States Patent [19]

Khosravi et al.

[11] Patent Number: 6,066,464
[45] Date of Patent: May 23, 2000

[54] IMMUNOASSAY OF IGF FAMILY OF PEPTIDES, THEIR BINDING PROTEINS AND RELATED MOLECULES IN DRIED WHOLE BLOOD FILTER PAPER SPOTS

[75] Inventors: M. Javad Khosravi, Toronto, Canada; Jehangir Mistry, League City, Tex.; Anastasia Diamandi, Toronto, Canada

[73] Assignee: Diagnostic Systems Laboratories, Inc., Webster, Tex.

[21] Appl. No.: 08/763,244

[22] Filed: Dec. 10, 1996

[51] Int. Cl.[7] .......................... G01N 33/53; G01N 33/537
[52] U.S. Cl. .............................. 435/7.9; 435/7.1; 435/7.8; 436/86
[58] Field of Search ................................ 435/7.8, 7.9, 7.1; 436/86

[56] References Cited

U.S. PATENT DOCUMENTS

| | | | |
|---|---|---|---|
| 4,224,031 | 9/1980 | Mee et al. ............................... | 23/230 B |
| 4,230,684 | 10/1980 | Pang et al. ................................ | 424/1 |
| 4,277,249 | 7/1981 | Broughton ................................ | 436/86 |
| 4,381,291 | 4/1983 | Ekins ........................................ | 424/1 |
| 4,431,743 | 2/1984 | Pang et al. ................................ | 436/542 |
| 4,455,381 | 6/1984 | Magnusson et al. ..................... | 436/543 |
| 5,096,812 | 3/1992 | Rachel et al. ............................. | 435/15 |
| 5,187,151 | 2/1993 | Clark et al. ................................ | 514/3 |
| 5,198,340 | 3/1993 | Mukku ...................................... | 435/7.8 |
| 5,204,267 | 4/1993 | Sangha et al. ............................ | 436/14 |
| 5,252,489 | 10/1993 | Macri ........................................ | 436/87 |
| 5,324,820 | 6/1994 | Baxter ....................................... | 530/350 |
| 5,432,097 | 7/1995 | Yourno ..................................... | 436/175 |
| 5,516,487 | 5/1996 | Rosenthal ................................. | 422/55 |
| 5,532,166 | 7/1996 | Ma ............................................ | 436/86 |
| 5,561,046 | 10/1996 | Baxter ....................................... | 435/7.1 |
| 5,641,682 | 6/1997 | Pagels et al. ............................. | 436/43 |

OTHER PUBLICATIONS

He Yu, et al. "Ultrasensitive Time–Resolved Immunofluorometric Assay of Prostate–Specific Antigen in Serum and Preliminary Clinical Studies." *Clinical Chemistry* 39(10):2108–2114 (1993).
Hannon, WH et al, WI NC997, vol.12(13) 26 pages, 1992.
Cassio, A, et al, Eur.J. Pediatrics, vol.145, pp. 187–189, 1986.
Mitchell, M.L et al, Pediatric Research, vol. 25(4), pp. 336–338, 1989.
Mitchell, M.L. et al, Clinical Endocrinology vol. 27, pp. 625–628, 1987.
Furlanetto, R.W., J. Clins. Endocrinology and Metabolism, vol. 54(5), pp. 1084–1086, 1982.
Cotterill, A.M. et al, Jan., Clinical Endocrinology, vol. 44(1), pp. 91–101, 1996.
Mauceri, H.J. et al, Nov.–Dec., Alcoholism: Clinical and Experimental Res., vol. 17(6), pp. 1201–1206, 1993.
Liu, F et al, Dec. 1994, J. of Clinical Endocrin. & Met. vol. 79(6), pp. 1883–1886.
Mitchell, M.L. et al, 1987, Clin. Chem., vol.33(4), pp. 536–538.
Westwood, M et al, Dec. 1994, J. Clin. Endocrin. & Metabol., vol. 79(6), pp. 1735–1741.
Mitchell, ML et al, Clin. Chem., 1987, vol. 33(4), pp. 536–538.
Liu, F et al, J. Clin. Endocrin. & Metabol. vol. 79(6), pp. 1883–1886, 1994.
Lewitt, MS et al, Jun. 1994, Endocrinol., vol. 134(6), pp. 2404–2409.
Chin, E et al, Endocrinol, vol. 134(6), Jun. 1994, pp. 2498–2504.
Lee, C.Y. et al, Endocrinol., vol. 136(11) Nov. 1995, pp. 4982–4989.
Bereket, A. et al, Clinical Endocrin., May 1996, vol. 44, pp. 525–532.
Scharf, J et al, Oct. 1995, J. of Hepatol., vol.23, pp. 424–430.
Scharf, J et al, Progress in Growth Factor Res., vol. 6, (2–4), pp. 175–180, 1995, Oct.
Barreca, A et al, Progress in Growth Factor Res., vol.6 (2–4), pp. 231–239, Feb. 1995.
Daughaday, WH. et al, Gen. Comp. Endocrinol., Aug. 1985, vol. 59(2), pp. 316–325.
Lord, A. P. D. et al, J. of Endocrinol., 1991, vol. 129, pp. 59–68.

*Primary Examiner*—James C. Housel
*Assistant Examiner*—Ginny Allen Portner
*Attorney, Agent, or Firm*—Jenkens & Gilchrist A Professional Corporation

[57] ABSTRACT

The present invention relates to screening or testing for insulin like growth factors, insulin like growth factor binding proteins and/or acid labile subunit by the use of a solid support. Blood is collected onto a solid support, such as paper, and subsequently the analytes of interest are extracted for testing.

12 Claims, 7 Drawing Sheets

IMMUNOASSAY OF IGF FAMILY OF PEPTIDES, THEIR BINDING PROTEINS AND RELATED MOLECULES IN DRIED WHOLE BLOOD FILTER PAPER SPOTS

BACKGROUND OF THE INVENTION

1. Field of the Invention

The present invention relates to screening or testing for insulin like growth factors and their binding proteins and related molecules ("IGF/IGFBPs"). More specifically the present invention relates to a method for screening IGF/IGFBPs from whole blood spotted on a solid support. Additionally, the present invention relates to a test kit for screening or testing IGF/IGFBPs on the solid support.

2. Description of the Prior Art

Insulin-like growth factors (IGFs) belong to a family of peptides that share a high degree of structural homology with insulin. IGFs (IGF-I and IGF-II) have important mitogenic and anabolic actions that are mediated by their binding to specific high affinity cell surface receptors (Jones J I, et al. Endocrin Rev 1995; 16:3–34). IGF-I and IGF-II are produced in multiple tissues and are present in blood and other biological fluids in association with specific high affinity IGF binding proteins (IGFBPs). Six structurally homologous IGFBPs with distinct molecular size, hormonal control, and tissue expression have been identified (Holly J M P, et al. Growth Regul 1994;4(suppl 1):20–30). Although the precise biological significant of the IGFBPs have not been clearly defined, they appear to play important roles in a complex system which modulates the bioavalability and functions of the IGFs. In addition, the ability of the IGFBPs to directly bind to cell surface receptors and trigger IGF-independent cellular functions have been recently reported (Cohen P, et al. Curr Opin Pediatr 1994;6:462–7). As used herein, the term "IGF/IGFBPs" refers to the IGFs, to IGFBPs and to acid labile subunit (ALS).

It is now well established that IGF-I is the major mediator of the in-vivo growth-promoting actions of growth hormone (GH) (Daughaday W H, et al. Endocrin Rev 1989;10:68–91). The IGFs circulate mostly (>85%) bound to an approximately 150 kD ternary protein complex consisting of IGFBP-3, the major serum IGFBP, and a unique, leucine-rich, acid-labile subunit (ALS). Smaller proportions of circulating IGFs are associated with other IGFBPs and less than 1% of serum IGF-I has been estimated to exist in an unbound or "free" form (Rosenfeld R G, et al. Recent Prog Horm Res 1990; 46:99–163).

The clinical assessment of growth hormone status has been controversial, primarily due to the episodic nature of GH secretion, its relatively short circulating half-life and considerable variability in GH measurement by different assay methods (Lee P D K, et al. Pediatr Res 1990; 27:45–51; Rosenfeld R G, et al. J Clin Endocrinol Metab 1995;80:1532–40). Currently, clinical evaluation of GH sufficiency invariably involves multiple venous blood sampling for the determination of pituitary GH secretion in response to a number of physiological or pharmacological stimuli. Because of the reported limitations of provocative GH testing which include arbitrary definition of diagnostic cut-off levels, and potential health risk and cost, alternative screening procedures have been sought. As blood IGF-I and IGFBP-3 (as well as ALS) levels are highly dependent on GH secretion, determination of their serum levels, individually or in combination, have been recently recognized as the most effective means in the evaluation of childhood GH deficiency (Rosenfeld R G, et al. J Clin Endocrinol Metab 1995;80:1532–40). Unlike growth hormone, the circulating levels of IGF-I and IGFBP-3 in the ternary molecular complex with ALS remain relatively constant, thus, allowing reliable determination of their concentrations in a single random specimen. More recently, measurement of IGFBP-2/IGF-I ratios have been reported to further enhance the diagnostic utility of IGF-I and IGFBP-3 measurements (Smith W J, et al. J Clin Endocrinol Metab 1993;77:1294–99).

In children, blood sampling by way of venipuncture has been problematic. Alternative procedure involves collection of blood by the less invasive and more convenient capillary puncture from the heel, finger or earlobe. Capillary blood dried on filter paper is a well established approach and has been successfully used in a number of large scale infant and population screening programs (Dussault Jh, et al. J Pediatr 1974;86:670–4; Augier D, et al. J Genet Hum 1985;33:325–36; Chanteau S, et al. Trans R Soc Trop Med Hyg 1989;83:414–6). The procedure allows collection of a relatively small volume of blood and has been regulated (Blood collection on filter paper for neonatal programs-2d ed.; Approved Standard. NCCLS publications LA4-A2. Villanova, Pa., 1992) to confer all the advantages of a reliable and safe specimen transportation system at a significantly low cost. The latter considerations may assume greater importance for applications requiring sample transportation to distant central laboratories and when transportation of liquid specimens may not be feasible and/or practical. The use of blood spots to enhance the stability of somatomedin is disclosed in U.S. Pat. No. 4,277,249 (Broughton).

We have recently described development of highly specific and simple non-competitive ELISA for reliable determination of IGF-I (Khosravi M J, et al. Clin Chem 1996; 42:1147–54), IGF-II (Diamandi A, et al. The Endocrine Soc 77th Ann Meeting 1995: P2-328), IGFBP-3 (Khosravi J, et al. Clin Chem 1996;S6:234), IGFBP-1 (Khosravi, J, et al. Clin Chem 1996;S6 171) and ALS in serum and other physiological fluids. The high affinity antibodies incorporated in these immunoassays have been selected for lack of cross-reactivity or interference by the closely related peptides or binding protein. However, because of the conserved nature of the IGF/IGFBPs, the immunoassays developed for human applications may be also useful for the analyte determination in other species. This may be of particular interest in veterinary medicine and livestock management where determination and monitoring of the IGFs and their binding proteins could have significant diagnostic or predictive values.

We here describe the first report on application of whole blood collected on filter paper in the analysis of the IGF/IGFBPs of human and veterinary interest. We demonstrate by example that blood dried on filter paper is ideal for the analysis of the IGF/IGFBPs as these analytes express high degree of stability in dried format and can be readily released from the solid-support by treatment with an appropriate elution reagent. Due to a naturally high concentrations of these analytes, their analysis in serum typically require a 50- to 100-fold sample pre-dilution. This requirement is advantageous as similar dilution factors could be incorporated in dried blood spot extraction procedures, thus, allowing employment of the current serum assays for the analysis of the extracted blood samples.

These and other advantages of the present invention will become apparent from the following detailed description.

SUMMARY OF THE INVENTION

The present invention provides a method of determining concentrations of an insulin-like growth factor or acid labile subunit in an individual comprising the steps of collecting blood having an unknown concentration of insulin-like growth factor or acid labile subunit from a subject; applying said blood onto a solid support; extracting blood from said solid support with a pre-extraction buffer to form a blood extract; contacting said blood extract with an acidification buffer, followed by a neutralization buffer to form a neutralized extract; and testing said neutralized extract for the concentration of insulin-like growth factor or acid labile subunit. The insulin-like growth factor may be IGF-I or IGF-II. The blood may be collected by capillary puncture. The capillary puncture may be finger prick, thumb prick or ear lobe prick.

Also provided in the present invention is a method of determining concentrations of an insulin-like growth factor binding protein or acid labile subunit comprising the steps of collecting blood having an unknown concentration of insulin-like growth factor binding protein from a subject; applying said blood onto a solid support; extracting blood from said solid support with a buffer extract to form a blood extract; and testing said blood extract for the concentration of insulin-like growth factor binding protein or acid labile subunit. The insulin-like growth factor binding protein may be IGFBP-1, -2, -3, -4, -5 or -6.

Also provided herein is a kit for measuring insulin-like growth factor, acid labile subunit, and/or insulin-like growth factor binding protein.

These and other advantages of the present invention will become apparent through the following detailed description.

BRIEF DESCRIPTION OF THE DRAWINGS

Paired dried blood spots (n=40) were extracted in two separate runs (Run 1 and run 2) by the direct acidification protocol FIG. (A) and the optimized IGFBP-3 extraction protocol FIG. (B) and analyzed. For each protocol, values obtained in Run 1 and Run 2 were compared. Run 1: y=0.19+0.89x (r=0.925); Run 2: y=0.33+0.79x (r=0.75).

Replicate dried blood spots were stored at various temperature and analyzed as indicated. Percent changes from the day 0 values are shown for three different runs.

Replicate dried blood spots were stored at various temperature and analyzed as indicated. Percent changes from the day 0 values are shown for three different runs.

Paired plasma and dried blood extracts from fresh blood samples (n=46) were analyzed for IGF-II. Correlation of values in plasma fraction vs those measured in dried blood extract are shown. y=118.79+0.69x (r=0.90).

Paired plasma and dried blood extracts from fresh blood samples (n=40) were analyzed for IGFBP-3. Correlation of values in plasma fraction vs those measured in dried blood extract are shown. y=3.4+0.95x (r=0.936).

DETAILED DESCRIPTION OF THE INVENTION

According to the teachings of the present invention, whole blood collected from an individual is spotted onto a suitable solid support. The whole blood is collected via techniques known to those skilled in the art including, but not limited to, finger prick, thumb prick, heel prick, ear lobe prick or any other form of capillary puncture by which a blood specimen may be obtained. In an alternative embodiment, whole blood may be obtained by venipuncture and spotted onto the solid support. Preferably, the blood specimen is collected via finger prick or thumb prick. Suitable devices for conducting capillary puncture include, but are not limited to, lancets and needles. Suitable lancets include, but are not limited to MONOLET® (SHERWOOD™ MEDICAL™, St. Louis, Mo., U.S.A.), TENDERFOOT® (BAXTER™, Miami, Fla., U.S.A.), MINILANCE®, AUTOLET®, UNILET®), and MICRO-LANCE® (BECTON DICKINSON™, Franklin Lakes, N.J., U.S.A.). The amount of whole blood required to be spotted onto the solid support is about 50 $\mu$L to about 200 $\mu$L, and preferably about 80 $\mu$L to about 100 $\mu$L. Accordingly, about 2 drops to about 4 drops may be spotted onto the solid support in accordance with the teachings of the present invention.

Any suitable form of solid support for collection may be used. A suitable solid support is one on which blood can be spotted and dried and from which IGF/IGFBPs can later be extracted. Preferably the solid support is a paper medium, and more preferably it is filter paper such as used in newborn screening programs and which are known to those skilled in the art. These include, but are not limited to SCHLEICHER and SCUELL™ ("S&S", Keene, N.H., U.S.A.) No. 903 filter papers. The S & S grade 903 filter paper is relatively thick and very absorbent, and applied drops of blood readily diffuse radially outward to form overlapping circles. It is the recognized standard for collecting dried blood, and the absorbency of each manufactured batch is kept within tight limits as certified by quality control testing carried out by the Centers for Disease Control and Prevention in Atlanta, Ga. (U.S.A.). This type of paper has been widely used in neonatal thyroid/phenylketonuria dried blood screening programs. In one embodiment, the solid support comprises a first area onto which blood is applied, and a second area for recordation of information about the blood donor. The second area need not have the absorbency of the first area, as blood will not be spotted onto the second area. Alternatively, the solid support comprises solely the first area described above. In such cases, information recordal can be conducted on a separate instrument.

After spotting, the blood is allowed to dry. Depending on ambient conditions, drying takes about one hour to about 3 hours, preferably about 2 hours. It is anticipated that the individual donor may be responsible for collecting the whole blood specimen, recording information about himself or herself or the test subject, and shipping or delivering the impregnated solid support to the diagnostic testing laboratory. The blood may be obtained from human or animal species. The animal species may include but are not limited to pig, cow, calf, goats, lamb, sheep, horse, chicken or marine species. The site of the blood drawn from animals could be those sites readily accessible and known to those skilled in the art.

Analysis of IGF/IGFBPs from the blood-impregnated solid support is conducted by first extracting the IGF/IGFBPs from the dried blood on the solid support. This may be accomplished by removing one or more sections from the blood-impregnated solid support. In an alternative embodiment, the entire blood-impregnated solid support may be subjected to extraction without removing one or more sections from said solid support. Those skilled in the art will know a suitable means of collecting such sections. Preferably, sections of about one (1) to about ten (10) millimeters diameter, and more preferably about six (6) to about seven (7) millimeters in diameter are removed from the blood-impregnated solid support. This may, for example, be conducted by using a single hole paper punch. But any other means for removing sections, such as knives or scissors, may be used.

The sections so removed, or, alternatively, the entire blood-impregnated solid support, are placed in a suitable container with an extraction buffer, and are incubated for a suitable time period in which the dried blood may be leached from the solid support and dissolved in the liquid phase. In the preferred embodiment, the extraction from the solid support of IGFs and ALS is conducted differently than the extraction of IGFBPs. However, a common blood extraction method may be developed for the IGFs/ALS and IGFBPs by those skilled in the art as briefly exemplified in this application (Example 4). The extraction protocol developed may or may not include an acidification-step, as dissociation of IGFs or ALS from IGFBPs may be accomplished by other means known to those skilled in the art and may include dissociating agents such as a variety of ionic or non-ionic detergents, organic or inorganic reagents, chelators, various salts such as NaCl, KCl, $MgCl_2$, $CaCl_2$ and other agents such as ATP and the like which may be capable of dissociating protein-protein complexes. The process may even include enzymatic degradation of one member of the complex for the purpose of releasing the binding partner of interest. Examples could include various specific or non-specific proteases known to those skilled in the art. These include, but are not limited to proteases such as trypsin, chymotrypsin, plasminogen, plasminogen activators and related molecules, and serine proteases such as prostate-specific antigen (PSA) used for the purpose of protein degradation.

For the IGFs and ALS, treatment with a suitable preextraction buffer is most preferable. Such treatment may, for example, be conducted by contacting the blood-impregnated solid support with a suitable preextraction buffer. Suitable pre-extraction buffers include any reagent or buffer solution as represented in Example 4. For example, reagents as simple as $dH_2O$ or solutions containing various concentrations of a number of buffering species may be used. These include but are not limited to Tris, borates, acetates, carbonates, phosphates or other buffering species known to those skilled in the art. The solid support is preferably contacted with the preextraction buffer for a period of about 30 minutes to about 2 hours, and most preferably about 1 hour, at which time the solid support may be removed from the extract. Following this, the extract is contacted with a suitable acidification buffer. Suitable acidification buffers include any acidifying agents capable of reducing the sample pH to a level needed to efficiently dissociate the IGF/IGFBPs/ALS complexes. These include but are not limited to the commonly used buffering species such as hydrocholoric acid, acetic acid, citric acid, or glycine-HCl. These also include other agents, buffers or compounds known to those skilled in the art. The extract is preferably contacted with the acidification buffer for a period of about 15 minutes to about 1 hour, and most preferably about 30 minutes. Following this, the extract is contacted with a suitable neutralization buffer. Suitable neutralization buffers include any neutralising agent known to those skilled in the art. These include but are not limited to buffers based on Tris, borates, acetates, carbonates and phosphates. These also include any other buffers or agent known to those skilled in the art. The extract is preferably contacted with the neutralization buffer for a period of about 15 minutes to about 1 hour, and most preferably about 30 minutes. Those skilled in the art will be able to ascertain a suitable volume of preextraction, acidification and neutralization buffers. Preferably they are about 0.1 ml to about 1.0 ml, and most preferably about 0.2 ml.

For the IGFBPs, preextraction is not needed. Instead, extraction is preferably conducted with a suitable extraction buffer. Suitable extraction buffers may include any reagent or buffer solution as represented in Example 4. For example, simple reagents such as $dH_2O$ or solution containing various concentrations of a number of buffering species may be used. These include, but are not limited to Tris, borates, acetates, carbonates, and phosphates. These also include other species known to those skilled in the art. For example, a buffer comprising 0.05 mol/L. sodium borate, pH 8.5, 9 g/L NaCl, 10 g/L bovine serum albumin, 0.1 g/L thimerosal is particularly effective. The extraction is conducted by contacting the blood-impregnated solid support with the extraction buffer for a period of about 15 minutes to about 1 hour, and most preferably about 30 minutes.

IGF/IGFBPs can be analyzed by any suitable sensitive assay technique. These include but are not limited to techniques such as immunoradiometric assays, chemiluminescence immunoassays, electroluminescence techniques, fluoroimmunoassays, enzyme immunoassays or bioluminescence immunoassays.

The methods and kits of the present invention can be used to measure IGF-1, IGF-II, IGFBP-1, IGFBP-2, IGFBP-3, IGFBP-4, IGFBP-5, IGFBP-6, ALS and other related molecules in both human and animal species. The present invention is of particular interest in veterinary medicine or in the livestock management industry, where determination and/or monitoring of the IGFs/IGFBPs/ALS may have significant diagnostic or predictive value for the selection and/or monitoring of the well being or the quality of the breeding stock. Samples may be collected from sites known to those skilled in the art. For example, blood samples from cows, pigs, goats and sheep may be collected via venous draw from sites such as, but not limited to, the jugular vein. Whole blood samples from rabbits may be collected from the ear vein. Blood samples from rats may be collected from heart puncture or tail clip. Whole blood samples from chickens may be collected from heart puncture or wing vein. For guinea pigs, orbital whole blood samples may be collected. Whole blood samples from fish may be collected from tail fins or gills. Other sites for collection of blood from various animal species may be used.

The present invention may be particularly useful when collection and transportation of liquid human or animal blood samples to distant laboratories, specifically to reference laboratories in other countries, may be prohibitive because of safety issues, cost or both. Furthermore, the present invention would significantly simplify the specimen storage requirements, especially when a large number of samples may be involved such as in screening programs or in cases of continuous livestock breeding monitoring and testing. In human applications, the method can be specifically used to diagnose disorders such as growth hormone deficiency in children and adults, acromegaly, as well as other abnormalities related to changes in production or utilization of IGF-I, IGF-II, IGFBP-1, IGFBP-2, IGFBP-3, IGFBP-4, IGFBP-5, IGFBP-6, ALS, related molecules or their concentration ratios. For example, there are currently examples of changes in the levels of IGFBP-1 in association with birthweight as well as changes in the circulating IGFBP-1 profile in conditions such as pregnancy, in patients with Laron's syndrome and insulin-dependent diabetes mellitus. Thus, measurement of IGFBP-1 for example may be useful in evaluating and monitoring fetal growth and development, pregnancy and in abnormal conditions associated with pregnancy.

The following examples serve to illustrate specific embodiments of the invention, but should not be considered as a limitation on the scope of the invention.

EXAMPLE 1

Whole blood collected by venipuncture in the presence of anticoagulants, primarily EDTA, were obtained from clinical laboratories in Canada. The samples were residuals from routine clinical test samples and were from an adult population. Blood collection filter paper cards (#903) were obtained from SCHLEICHER and SCHUELL (S & S), Keen, N.H. The paper has been manufactured according to the specifications set by the National Committee for Clinical Laboratory Standards (NCCLS) for blood collection. All other chemical reagents were of highest quality and were obtained from SIGMA CHEMICAL CO.™, St. Louis, Mo., or Amresco, Inc., Solon, Ohio. Forty eight well cell culture plates were products of COSTAR™, Cambridge, Mass.

Precollected blood samples were thoroughly mixed before application to filter paper or use in liquid-phase whole blood sample analysis. Blood spots were prepared by applying one drop of blood with a disposable pipet onto the designated circular area on the filter paper and allowed to air dry at room temperature overnight. The dried blood spots were stored in a plastic bag at room temperature unless otherwise indicated.

For collection of plasma, blood samples used for spotting were allowed to stand at room temperature for 2–4 h and samples of plasma were carefully transferred to corresponding sample tubes. The plasma samples not assayed immediately were stored at −20° C. and used for these studies within 1–2 weeks after collection.

All analysis were performed using a single ¼ inch diameter dried blood filter paper spot disc with an impregnation whole blood volume of approximately 13 $\mu$L. The blood spot disc was punched out by a manual paper puncher from an area that was completely impregnated with blood. The disc was placed into a well of a 48 well cell culture plate (total well volume 1.6 mL), and the blood was extracted into a liquid-phase for the measurement of IGF/IGFBPs.

The concentration of IGF-I, IGF-II, IGFBP-2, IGFBP-3, and IGFBP-1 in plasma, filter paper extracts or whole blood were measured by immunoassay kits manufactured and marketed by the Diagnostic Systems Laboratories (DSL™, Webster, Tex.). All the assays except for IGFBP-2 were based on non-competitive ELISA principles involving a solid-phase capture antibody and a soluble horseradish peroxidase (HRP)-labeled detection antibody. All assays were performed according to the manufacturer's instructions. The procedures for analyte determination in whole blood or plasma was exactly as described for serum using the same sample volume. A brief description of the assays is as follows:

The DSL™ Direct IGF-I and IGF-II ELISA kits are performed in a two-step format, involving anti-IGF-I or anti-IGF-II antibody coated microwells and a pairing anti-IGF-I or anti-IGF-II detection antibody labeled with HRP. The IGFs' direct ELISAs incorporates a sample pre-treatment step to dissociate the IGFs from their binding proteins. This involves incubation of 20 $\mu$L of serum samples with 1.0 mL of the IGF Acidification Buffer, followed by 30 min room temperature incubation and addition of 1.0 mL of the Neutralization Buffer which raises the pH to slightly alkaline and blocks reassociation of IGFs with IGFBPs. The final sample preparation dilution factor is 101-fold and 20 $\mu$L is used for IGF-I or IGF-II analysis. The IGF-I kit has a total incubation time of <3 h, a standard range of 0.1 to 6 ug/L (10–606 ug/L after correction for the sample pre-treatment dilution factor) and an overall precision of <10%. The IGF-II kit has a total incubation time of <3 h, a standard range of 0.5 to 15 ug/L (51–1515 after correction for the sample pre-treatment dilution factor) and an overall precision of <10%.

The DSL™ IGFBP-3 ELISA kit is a dual-epitope, two-step immunoassay, performed in anti-IGFBP-3 coated microwells. The assay requires a 100-fold serum sample pre-dilution with the zero standard to bring the IGFBP-3 levels within the measuring range of the assay. The IGFBP-3 ELISA uses a sample volume of 25 $\mu$L, a total incubation time of ~3 h, a standard range of 2 to 100 ug/L, and an overall precision of <10%.

The DSL™ IGFBP-2 is based on the radioimmunoassay (RIA) principle, involving $^{125}$I-labeled IGFBP-2 tracer and limited amount of a highly specific anti-IGFBP-2 antibody. The assay requires a 50-fold serum sample pre-dilution with the zero standard to bring the IGFBP-2 levels within the measuring range of the assay. The IGFBP-2 RIA uses a sample volume of 200 $\mu$L, a total incubation time of $\mu$24 h, a standard range of 2.5 to 100 ug/L, and an overall precision of <10%. Radioactivity was measured by the LKB 1275 MINIGAMMA COUNTER,™ PHARMACIA LKB BIO-TECHNOLOGY ABe™, Uppsala, Sweden.

The DSL™ Total IGFBP-1 ELISA kit is a dual-epitope, two-step immunoassay, performed in anti-IGFBP-1 coated microwells. The assay measures total IGFBP-1 levels, in a 25 $\mu$L sample volume in <2 h total incubation time. The assay has a dynamic range of up to 160 $\mu$g of IGFBP-1/L and an overall precision of <10%.

Optical density measurements for all ELISAs were performed with the Labsystems Multisken Multisoft microplate reader (Labsystems, Helsinki, Finland).

EXAMPLE 2

Extraction of IGF-I

Determination of IGFs require their dissociation from IGFBPs. Procedures for direct measurement of IGFs by sample acidification to a pH of about 2.0 to dissociate the complexes followed by neutralization to slightly alkaline pH prior to analysis have been developed by DSL™. Thus, the optimized IGF-I extraction protocol combined a pre-extraction step with sample acidification and neutralization steps using the corresponding reagents developed for direct analysis of the IGFs by DSL™. Two hundred µL of the IGF pre-extraction buffer (see below) was added to each well containing a single unknown or control dried blood disc and incubate shaken at room temperature for 1 h to allow complete elution of IGF from the filter paper. To the extract was then added 200 µL of an acidification buffer, containing 0.4M glycine-HCl, pH 2.0 incubated as above for 30 min, and neutralized by adding 400 µL of a neutralization buffer, containing 0.85M Tris and 0.1% sodium dodecylsulfate. The extract was mixed for 2 min and used for IGF-I analysis. The extracts could be used for the measurement of IGF-II and ALS as these analytes also require dissociation from IGFBPs prior to analysis. EXAMPLE 3

Extraction of IGFBP-3

For the optimized IGFBP-3 extraction, 0.5 mL of the IGFBP-3 extraction buffer (see below) was added to each well containing a single unknown or control dried blood disc. IGFBP-3 was eluted by incubating the wells shaken for 1 h at room temperature. The extract was used for IGFBP-3 determination as well as determination of IGFBP-2 which is similarly released into the surrounding media. The same extraction procedure was used for elution of IGFBP-1 from dried blood filter paper spots, except that discs were extracted with 0.25 mL of the IGFBP-3 extraction buffer. EXAMPLE 4

Optimization of the Extraction Procedures

Extraction efficiency of IGF-I and IGFBP-3 was investigated using a number of extraction media and extraction time (30–120 min). The extraction media used were as follows: (1), deionized water (dH$_2$O); (2), IGF-I pre-extraction buffer (0.005 mol/L Tris, pH 7.0, 0.5 mL/L Tween-20); (3), IGFBP-3 extraction buffer (0.05 mol/l, sodium borate, pH 8.5, 9 g/L NaCl, 10 g/l, bovine serum albumin (BSA), 0.1 g/L thimerosal); (4) 0.05 mol/L sodium phosphate, pH 7.4, 0.9 g/L NaCl, 10 g/L BSA, 1 mL/L Tween-20, 0.1 g/L thimerosal.

To explore the possibility of using a common extraction procedure and reagents for IGF-I and IGFBP-3, dried blood spot discs were also directly extracted by the addition of 0.5 ml of the IGF acidification buffer/well followed by 1 h incubation as above and addition of 0.5 mL of the IGF neutralization buffer and mixing. The performance of the direct acidification protocol for IGF-I and IGFBP-3 analysis was then evaluated.

Both IGF-I and IGFBP-3 were almost completely released within 30 min of incubation (Table 1), and all extraction buffers including dH$_2$O appeared equally effective (Table 2).

TABLE 1

Kinetics of IGF-I (ug/L) and IGFBP-3 (mg/L) Extraction from Dried Filter Paper Blood Spot

| | IGF-I Extraction Time (min) | | | IGFBP-3 Extraction Time (min) | | |
|---|---|---|---|---|---|---|
| Sample | 30 | 60 | 120 | 30 | 60 | 120 |
| 1 | 42 | 66 | 71 | 4.9 | 5.2 | 4.7 |
| 2 | 167 | 173 | 172 | 2.6 | 2.7 | 2.7 |
| 3 | 103 | 101 | 88 | 5.0 | 5.2 | 5.0 |
| 4 | 200 | 197 | 216 | 3.2 | 3.3 | 3.5 |
| 5 | 133 | 137 | 140 | 9.3 | 9.4 | 9.7 |
| 6 | 57 | 67 | 69 | 1.9 | 2.4 | 2.3 |
| 7 | 88 | 80 | 78 | 2.7 | 2.5 | 2.9 |
| 8 | 167 | 201 | 205 | 4.3 | 4.5 | 4.8 |

TABLE 2

Effect of Various Reagents on IGF-I (ug/L) and IGFBP-3 (mg/L) Extraction Efficiency

| | IGF-I Extraction Media[a] | | | | IGFBP-3 Extraction Media | | | |
|---|---|---|---|---|---|---|---|---|
| Sample | 1 | 2 | 3 | 4 | 1 | 2 | 3 | 4 |
| 1 | 179 | 178 | 185 | 138 | 2.00 | 2.34 | 1.94 | 2.20 |
| 2 | 97 | 67 | 72 | 85 | 1.94 | 2.20 | 2.23 | 2.12 |
| 3 | 138 | 123 | 129 | 136 | 0.81 | 1.05 | 0.83 | 0.83 |
| 4 | 96 | 88 | 75 | 79 | 0.92 | 1.02 | 0.97 | 1.02 |
| 5 | 131 | 133 | 104 | 118 | 1.80 | 1.84 | 1.92 | 1.65 |

[a]1–4 indicate extraction media: (1), deionized water (dH$_2$O); (2), IGF-I pre-extraction buffer (0.005 mol/L Tris, pH 7.0, 0.5 mL/L Tween-20); (3), IGFBP-3 extraction buffer (0.05 mol/L sodium borate, pH 8.5, 9 g/L NaCl, 10 g/L bovine serum albumin (BSA), 0.1 g/L thimerosal); (4) 0.05 mol/L sodium phosphate, pH 7.4, 0.9 g/L NaCL, 10 g/L BSA, 1 mL/L Tween-20, 0.1 g/L thimerosal.

Figure 1A:
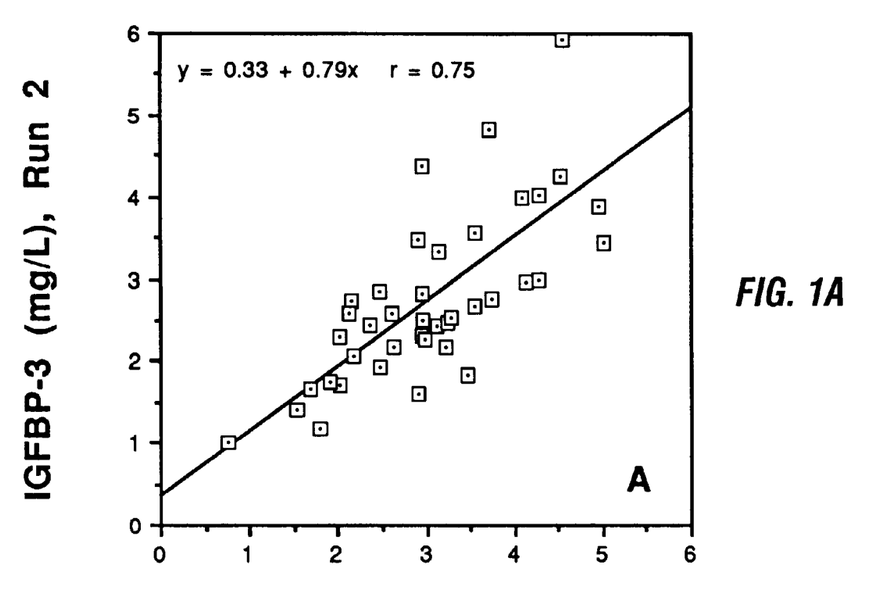
FIGS. 1A & B. Interassay assay correlation of IGFBP-3
Figure 1B:
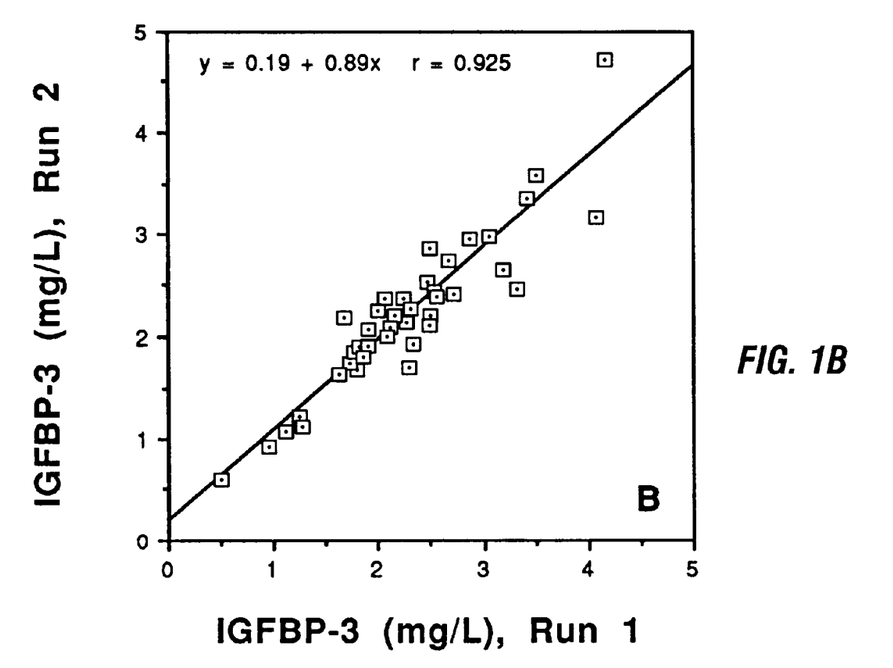

Although, the IGF acidification buffer could be used for the development of a common extraction method, the procedure appeared less promising. Compared to the optimized IGF-I and IGFBP-3 extraction methods, the direct acid-extraction approach showed significant variation in extraction kinetics, as evaluated for IGF-I (Table 3), and in between-run reproducibility of IGFBP-3 dried blood extraction performed on two different occasions (FIG. 1).

TABLE 3

Effect of Direct Acidification on IGF-I (µg/L) Dried Blood Spot Extraction Kinetics

| | IGF-I Extraction Time (min) | | |
|---|---|---|---|
| Sample | 30 | 60 | 120 |
| 1 | 267 | 343 | 316 |
| 2 | 87 | 103 | 53 |
| 3 | 240 | 263 | 185 |
| 4 | 184 | 186 | 121 |
| 5 | 553 | 499 | 526 |
| 6 | 150 | 100 | 107 |
| 7 | 157 | 125 | 150 |
| 8 | 194 | 114 | 129 |

The efficiency of the optimized extraction methods was evaluated by comparing whole blood concentrations of IGF-I and IGFBP-3 with those obtained from extracts of the corresponding dried blood spots. For these analysis, 10 µL aliquot of 6 different freshly drawn blood samples were spotted, dried overnight, and the extracts of the entire 1 µL blood spots were analyzed along with 10 µL of the appropriately processed original whole blood samples. As shown in Table 4, the recovery of IGF-I and IGFBP-3 ranged from 87%–107%, and 91 %–109%, with mean values of 97% and 101%, respectively.

TABLE 4

Recovery of IGF-I and IGFBP-3 from Dried Filter Paper Blood Spot

| Sample | IGF-I (ug/L) | | | IGFBP-3 (mg/L) | | |
|---|---|---|---|---|---|---|
| | Blood | Extract | % Recovery | Blood | Extract | % Recovery |
| 1 | 96 | 90 | 94 | 2.2 | 2.0 | 91 |
| 2 | 242 | 241 | 100 | 4.3 | 3.9 | 91 |
| 3 | 33 | 33 | 100 | 2.0 | 2.2 | 110 |
| 4 | 123 | 134 | 92 | 3.4 | 3.4 | 100 |
| 5 | 301 | 280 | 107 | 4.4 | 4.8 | 109 |
| 6 | 405 | 465 | 87 | 4.5 | 4.8 | 107 |

The extraction efficiency of IGF-I and IGFBP-3 was unaffected by changes in the volume of the extraction buffers. Replicate dried blood spots of two representative samples extracted with 0.15 to 0.6 mL of the IGF-I pre-extraction buffer followed by addition of proportional volumes of the acidification and neutralization solutions, as described IGF-I extraction, gave a mean recovery of 97±8.2% in comparison to the value obtained by the usual IGF-I extraction protocol (Table 5). Similarly, the mean recovery of IGFBP-3 from dried blood extracted with 0.25 to 2.0 mL of the extraction buffer was 107±6.1% in comparison to its concentration measured by the optimized IGFBP-3 extraction protocol (Table 6).

TABLE 5

Effect of Extraction Buffer Volume on IGF-I (ug/L) Dried Blood Filter Paper Assay

| Extraction volume | Sample 1 | | Sample 2 | |
|---|---|---|---|---|
| (mL) | Recovered | % Recovery[a] | Recovered | % Recovery[a] |
| 0.6 | 241 | 91 | 315 | 84 |
| 0.8[b] | 265 | 100 | 375[b] | 100 |
| 1.2 | 269 | 101 | 369 | 99 |
| 1.6 | 264 | 99 | 368 | 99 |
| 2.4 | 240 | 90 | 411 | 111 |

[a]Recovery calculated as % of value measured with optimized extraction protocol
[b]Values by the optimized extraction protocols

TABLE 6

Effect of Extraction Buffer Volume on IGFBP-3 (mg/L) Dried Blood Filter Paper Assay

| Extraction volume | Sample 1 | | Sample 2 | |
|---|---|---|---|---|
| (mL) | Recovered | % Recovery[a] | Recovered | % Recovery[a] |
| 0.25 | 4.5 | 105 | 3.5 | 100 |
| 0.5[b] | 4.3 | 100 | 3.5[b] | 100 |
| 0.75 | 4.7 | 109 | 4.0 | 114 |
| 1.0 | 4.7 | 109 | 3.6 | 103 |
| 1.5 | 4.3 | 100 | 4.1 | 117 |
| 2.0 | 4.8 | 112 | 3.9 | 111 |

[a]Recovery calculated as % of value measured with optimized extraction protocol The combined reproducibility of dried blood sample extraction and analysis for IGF-I and IGFBP-3 from three different samples are shown in Table 7. Intra-assay precision for IGF-I, which also include between-spot extraction variations, was evaluated by replicate analysis (n=12) of extracts obtained from 3–6 separate blood spots. Inter-assay precision was established by duplicate analysis of 7 separate dried blood spot extracts assayed in 7 separate runs. For determination of IGFBP-3 intra-assay precision, 12 separate spots were extracted and the extracts analyzed in duplicate (n=24). The IGFBP-3 inter-assay CVs were derived from duplicate analysis of 5 separate blood spot extracts in 5 separate assays.

TABLE 7

Precision of Dried Filter Paper Blood IGF-I (ug/L) and IGFBP-3 (mg/L) Assay

| Sample | IGF-I, | | IGFBP-3 | |
|---|---|---|---|---|
| | Intra-assay Mean ± % CV | n | Intra-assay Mean ± % CV | n |
| 1 | 126 ± 8.5 | 12 | 1.65 ± 8.7 | 24 |
| 2 | 320 ± 8.5 | 12 | 2.00 ± 8.0 | 24 |
| 3 | 526 ± 5.4 | 12 | 8.10 ± 8.0 | 24 |
| 1 | 99 ± 16.7 | 7 | 0.92 ± 11.7 | 5 |
| 2 | 229 ± 5.3 | 7 | 4.87 ± 4.7 | 5 |
| 3 | 420 ± 12.1 | 7 | 3.08 ± 6.2 | 5 |

Figure 2A:
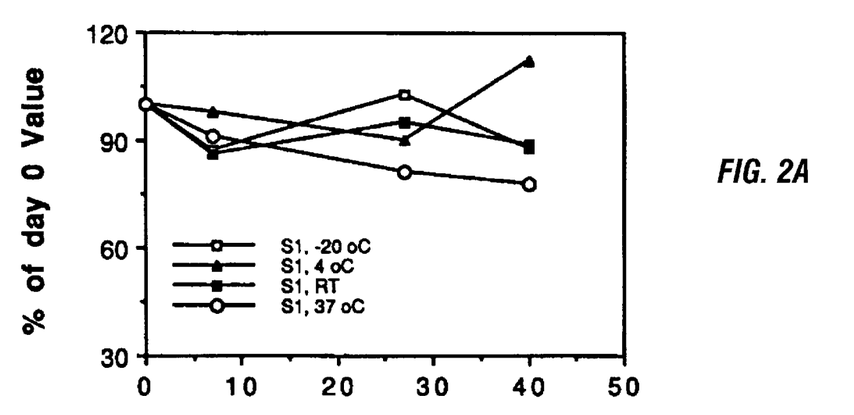
FIGS. 2A & B & C. Stability of IGF-I in dried blood filter paper spots
Figure 2B:
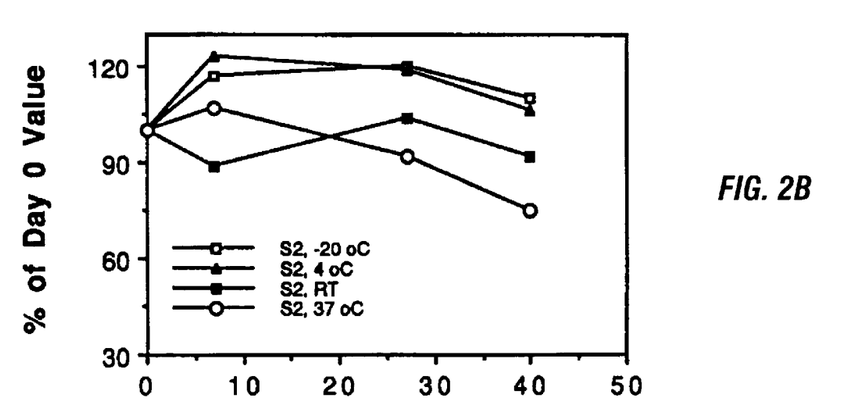
Figure 2C:
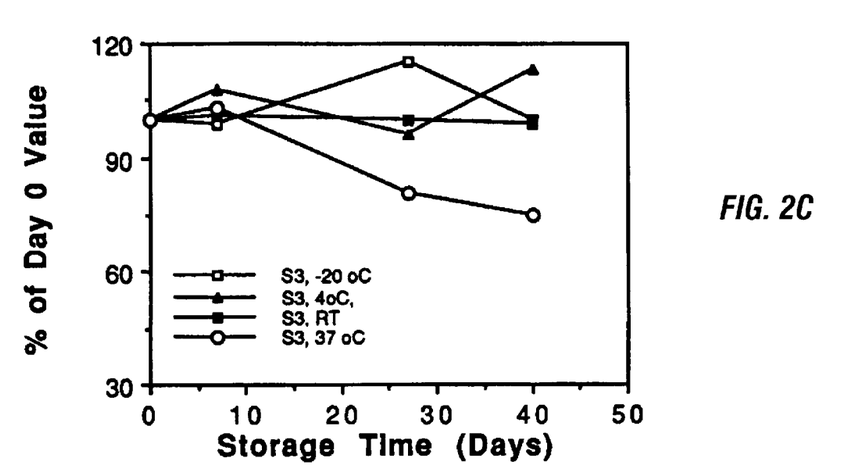
Figure 3A:
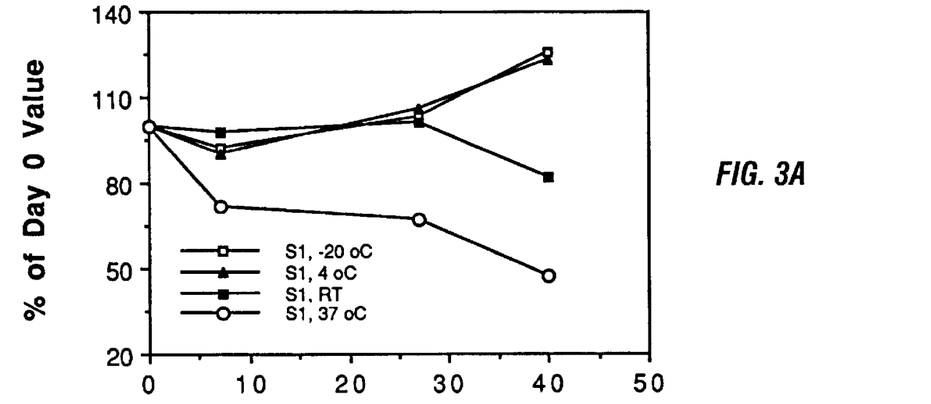
FIGS. 3A, B & C. Stability of IGFBP-3 in dried blood filter paper spots
Figure 3B:
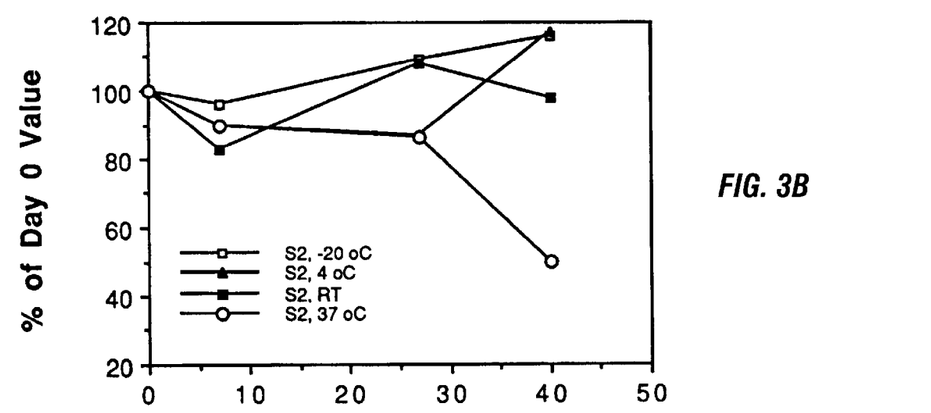
Figure 3C:
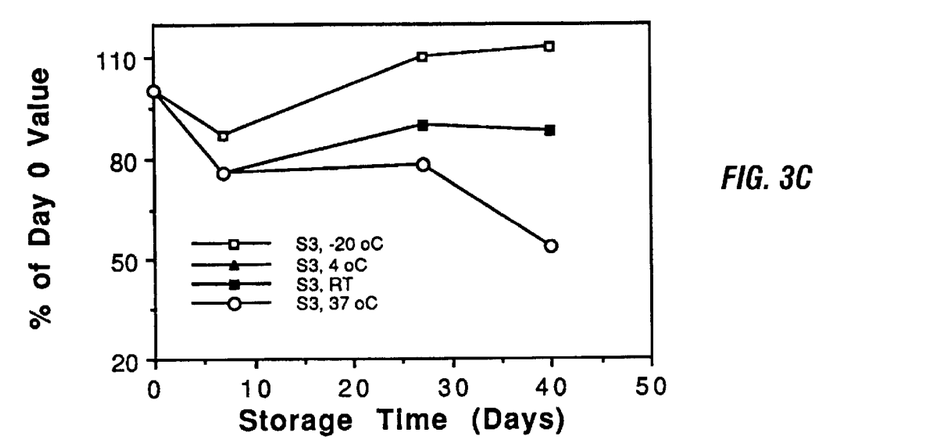

IGF-I and IGFBP-3 demonstrated high stability in dry form. Replicate dried blood filter paper spots from three different specimen with wide concentration range were prepared and stored at four different temperatures The blood spots' IGF-I and IGFBP-3 were measured at 0, 8, 27 and 40 days of storage. For both analytes, the recovery at room temperature, 4° C. and −20° C. were >80% of the zero day value at 40 days of storage. The recovery of IGF-I and IGFBP-3 after 27 days of storage at 30° C. exceeded 80% and 67%, respectively (FIGS. 2 and 3). FIGS. 2 and 3 depict three replicate experiments each. In both Figures, the open squares represent storage at −20° C.; the triangles represent storage at 4° C.; the closed squares storage at room temperature; and the open circles storage at 37° C.

As outlined above, the measurement of the plasma levels of IGFs, IGFBP-2, and IGFBP-3 require a 50- to 100-fold sample dilution to bring them within the measuring range of the assays. To simplify the calibration requirement of measuring these analytes in dried blood filter paper extract, we incorporated a similar dilution factor in the extraction procedures to permit employment of the current kits' calibrators. With this approach, the levels of the analyte measured in plasma and in the corresponding blood extract would be expected to correlate with a slope value representing their respective dilution factors. For example, in both IGF-I and IGFBP-3 ELISAs, plasma samples are diluted by about 100-fold while, assuming a hematocrit of 50% and a disc blood volume of 13 $\mu L$, the fractional plasma volume of the spotted blood is diluted by approximately 123- and 77-fold for IGF-I and IGFBP-3, respectively. Therefore with use of the same liquid standards, the IGF-I levels measured in the dried blood extracts should be ideally less than those measured in plasma (by ~10–20%), while the IGFBP-3 levels should be higher by about 10–20%. It is, however, possible to adjust the extraction buffer volume (or the standards) to obtain closely comparable values.

EXAMPLE 5

Distribution of IGF-I and IGFBP-3 in whole blood

A freshly collected whole blood EDTA sample was aliquoted into several fractions of equal volumes and centrifuged, except for one fraction representing the originally drawn whole blood sample. The relative volume of the plasma portion of the centrifuged fractions was then changed to create a set of whole blood samples with varying degree of hematocrit. After mixing, the IGF-I and IGFBP-3 levels in the plasma and the resulting whole blood samples were measured and compared to their corresponding hematocrit values (hematocrit ranged from 0.20 to 0.70). Briefly, the measured IGF-I or IGFBP-3 levels in each blood fraction was compared to the plasma IGF-I or IGFBP-3 concentration and a whole-blood to plasma IGF-I and IGFBP-3 concentration ratios were established. These ratios were then compared to the fractional plasma volume of the whole blood samples calculated as 1 minus the hematocrit value (1-hematocrit). Comparable results were taken to indicate presence of IGF-I and IGFBP-3 within the plasma portion.

The whole blood fractions prepared as above with hematocrits ranging from 0 (plasma) to 0.70 were spotted onto filter paper, dried and extracted for IGF-I and IGFBP-3 analysis. The concentrations of IGF-I and IGFBP-3 in the whole blood fractions and the spot extracts were measured. The percent change in the whole blood values from that obtained for the original whole blood sample was calculated as recently described (Hoffman, B R, et al. Clin Chem 1996;42:536–44). Similarly, the percent change in the extracted blood spots values from the corresponding value of the original whole blood spot extract was calculated. The differences in the effect of hematocrit on the analyte concentrations measured in whole blood or extracts of whole blood were compared.

Circulating molecules may be differentially distributed among whole blood subfractions (plasma and red blood cell fractions) whose relative fractional volumes are subject to change, both within- and between-individuals. As these variables could significantly alter the validity of the whole blood measurements, we investigated distribution of the representative components of the IGF/IGFBPs. IGF-I and IGFBP-3 were measured in plasma and in a series of corresponding whole blood fractions with hematocrit ranging from 0.20 to 0.70. As shown in Table 8, the whole blood levels of IGF-I and IGFBP-3 varied by ~3–4 fold as a function of variations in hematocrit. However, the magnitude of changes in whole blood levels were inversely related to hematocrit, suggesting distribution of IGF-I and IGFBP-3 in the plasma fraction. Furthermore, comparison of whole blood/plasma concentration ratios for IGF-I and IGFBP-3 with the corresponding fractional plasma volume of each blood sample (calculated as 1-Hematocrit) showed closely comparable relationship (Table 9).

TABLE 8

Hematocrit Effect on Measured IGF-I, and IGFBP-3 Whole Blood and Extracts Levels

| Hematocrit | IGF-I (ug/L) | | IGFBP-3 (mg/L) | |
|---|---|---|---|---|
| | WB[a] | Extract | WB | Extract |
| 0.70 | 92 | 155 | 0.8 | 2.7 |
| 0.62 | 134 | 153 | 1.4 | 3.6 |
| 0.434 | 200 | 223 | 2.3 | 4.5 |
| 0.33 | 234 | 210 | 2.8 | 4.4 |
| 0.27 | 240 | 216 | 3.1 | 4.9 |
| 0.20 | 287 | 220 | 3.5 | 4.6 |
| 0 (plasma) | 312 | 217 | 4.5 | 4.6 |

[a]WB = Whole blood

TABLE 9

Comparison of Whole Blood/Plasma Concentration Ratio with Fractional Plasma Volume[a]
Whole Blood/Plasma Concentration Ratio

| 1-Hematocrit | IGF-I | IGFBP-3 |
|---|---|---|
| 0.3 | 0.29 | 0.18 |
| 0.38 | 0.43 | 0.31 |
| 0.57 | 0.64 | 0.51 |
| 0.67 | 0.75 | 0.62 |
| 0.73 | 0.77 | 0.69 |
| 0.80 | 0.91 | 0.78 |

[a]Defined as 1-hematocrit

To quantify the effect of hematocrit, IGF-I and IGFBP-3 levels were measured in the whole blood fractions described above and in their corresponding dried blood extracts. In both series of samples, the measured values were calculated as percent change from the corresponding value obtained for the originally drawn 0.33 hematocrit specimen. As expected for analytes present primarily in the plasm fraction, variation in hematocrit had a significant effect on IGF-I and IGFBP-3 levels measured in whole blood (Table 10). The whole blood concentrations of these analytes changed by ~8–10% for every 0.05 unit change in hematocrit. In contrast, the effect of variation in hematocrit on the analyte concentrations measured in the dried blood filter paper extracts were comparatively less pronounced. The IGF-I and IGFBP-3 levels changed by ~2–4% per 0.05 unit change in hematocrit. Only at abnormally high hematocrit (>0.6), the change in blood extract concentrations relative to those measured in the corresponding 0.33 hematocrit specimen were >10%.

EXAMPLE 6

Analyte Determination in Plasma and Corresponding Whole Blood and Dried Blood Extract Fresh EDTA-whole blood samples (n=46) were spotted on filter paper, dried overnight, and extracted according to the protocols described for filter paper extraction of IGF-I and IGFBP-3. The corresponding whole blood and /or plasma fractions were also processed for IGF-I, IGF-II, IGFBP-2 and IGFBP-3 determination as described above and in their respective DSL ELISA or RIA protocols.

Figure 4A:
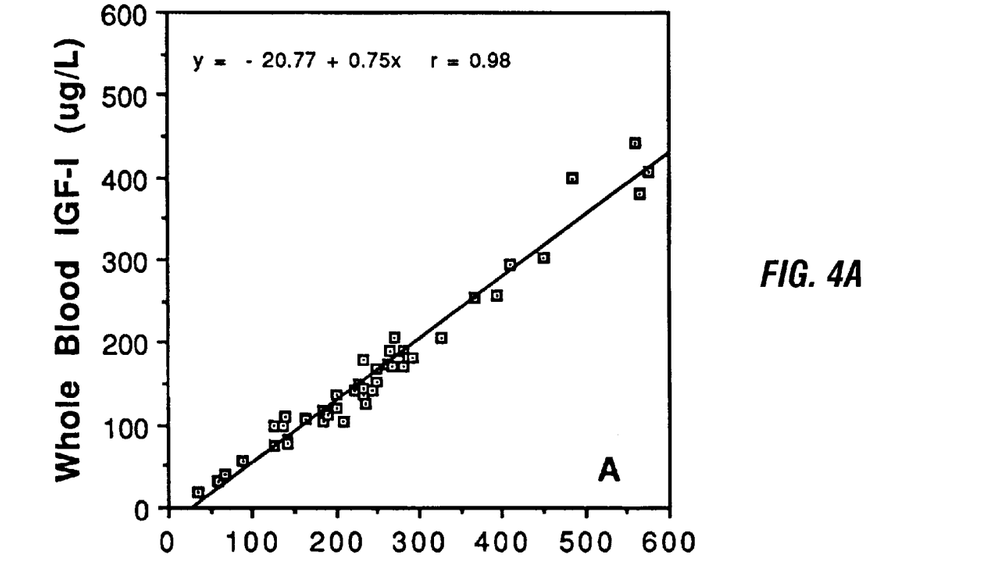
FIGS. 4A & B. Comparison of IGF-I in plasma, whole blood and dried blood extracts Corresponding whole blood, plasma and dried blood extracts from fresh blood samples (n=46) were analyzed for IGF-I. Correlation of values in plasma fraction vs those measured in whole blood FIG. (A) and dried blood extract FIG. (B) are shown. A: y=−20.77+0.75x (r=0.98); B: y=−7.7+0.81x (r=0.98).
Figure 4B:
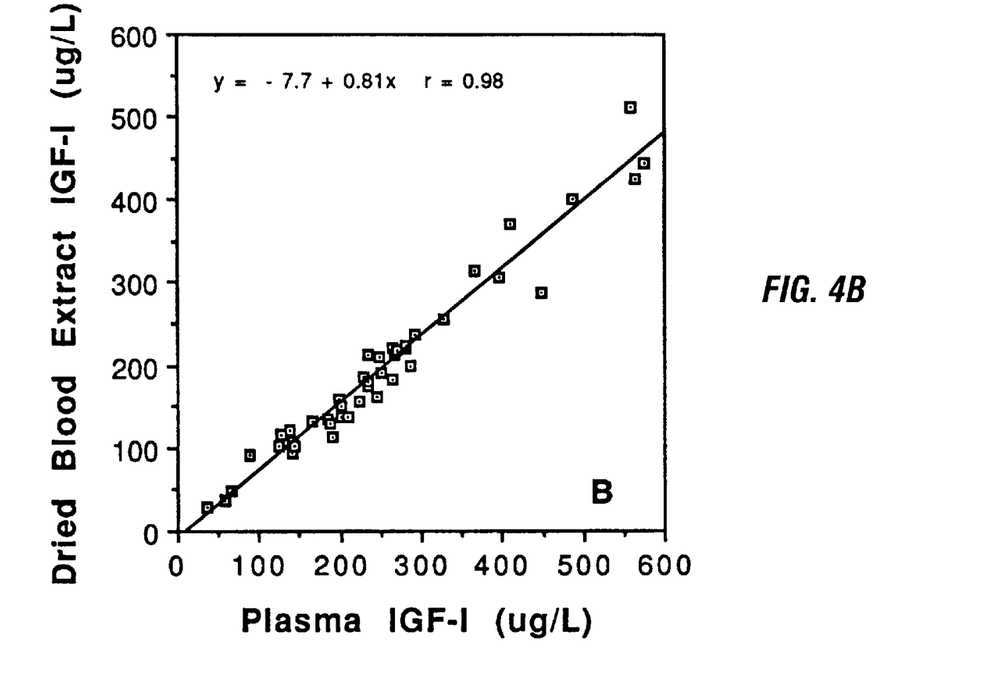
Figure 5A:
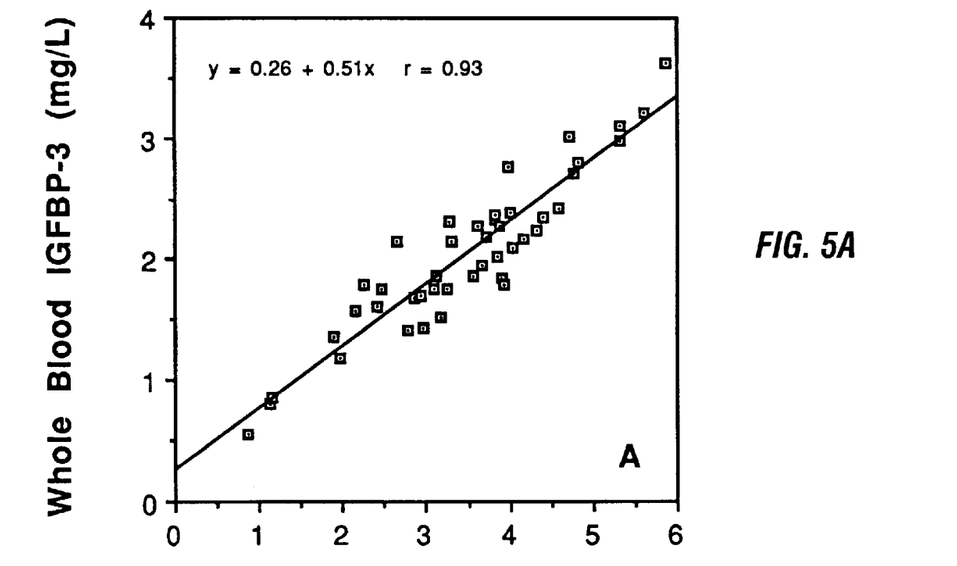
FIGS. 5A & B. Comparison of IGFBP-3 in plasma whole blood and dried blood extracts Corresponding whole blood, plasma and dried blood extracts from fresh blood samples (n=46) were analyzed for IGFBP-3. Correlation of values in plasma fraction vs those measured in whole blood FIG. (A) and dried blood extract FIG. (B) are shown. A: y=0.26 0.51x (r=0.93); B: y=0.25+1.03x (r=0.944).
Figure 5B:
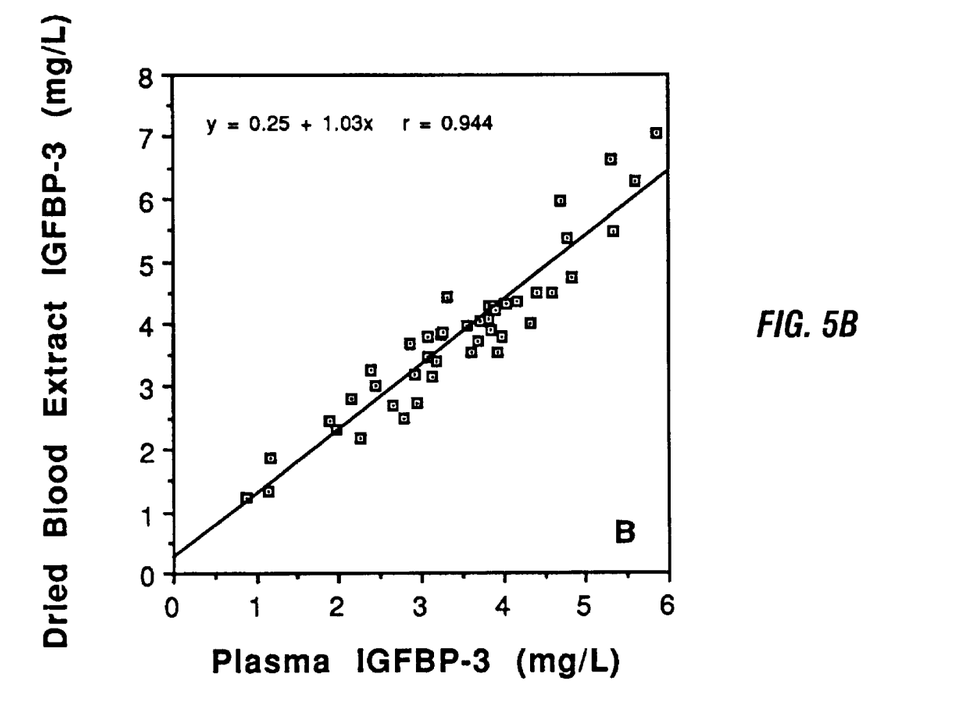
Figure 6:
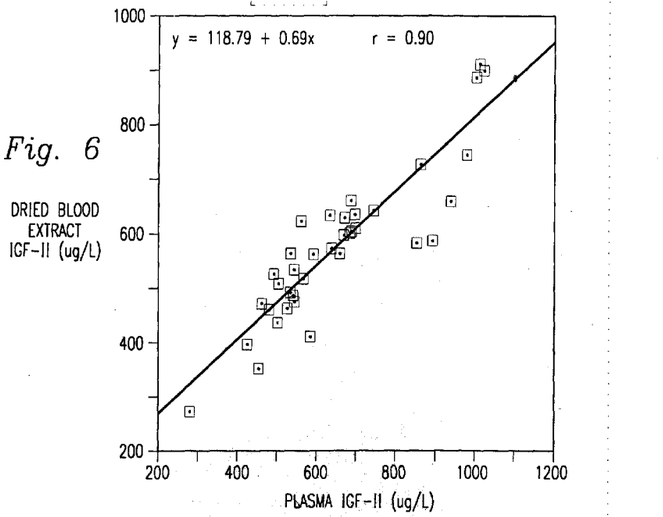
FIG. 6. Comparison of IGF-II in plasma and dried blood extracts
Figure 6A:
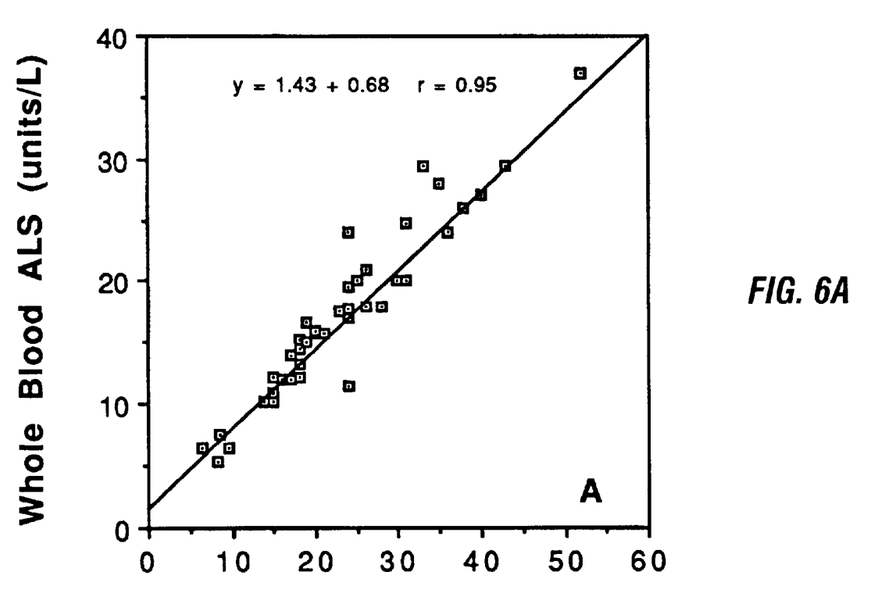
Figure 6B:
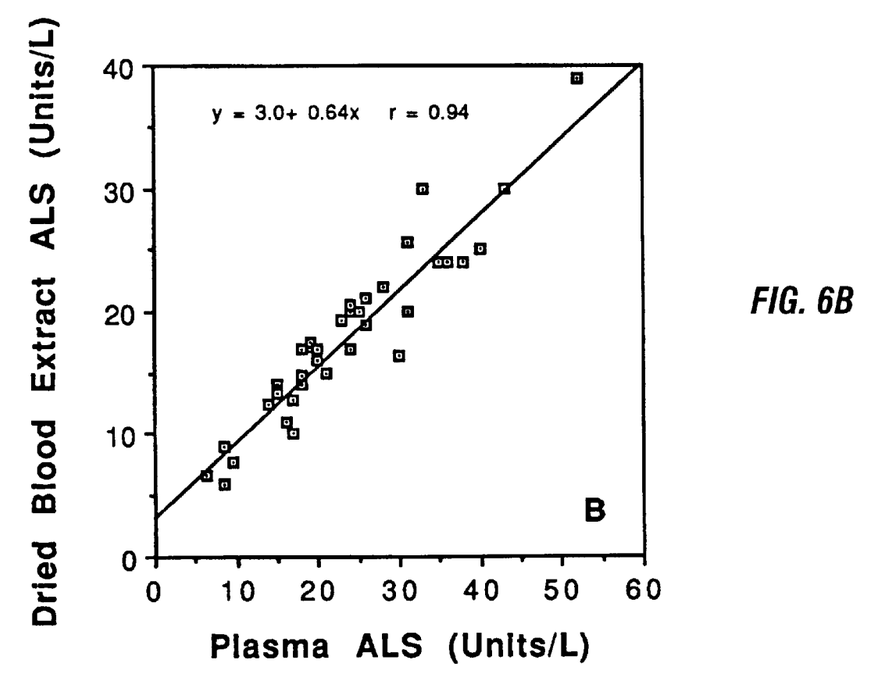
Figure 7:
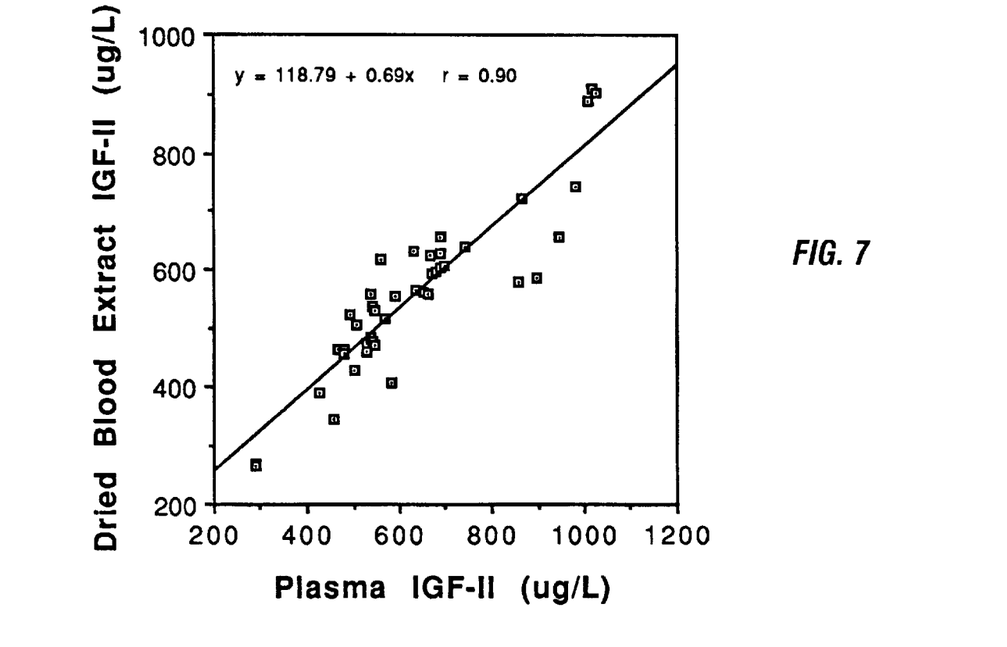
FIG. 7. Comparison of IGFBP-2 in plasma and dried blood extracts
Figure 8:
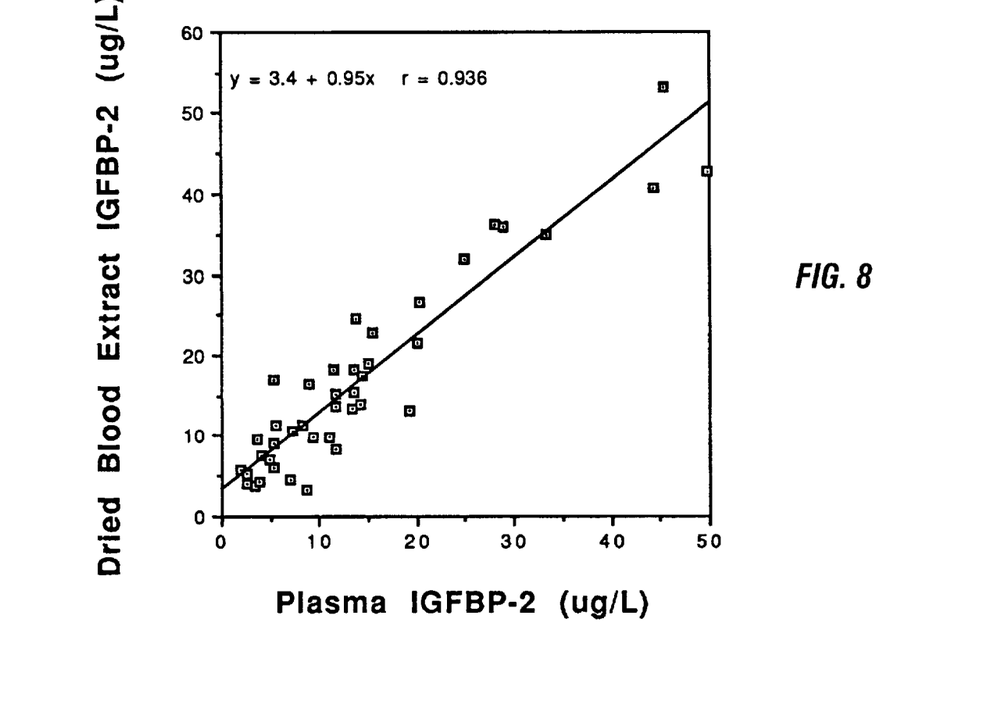
FIG. 8. Comparison of IGFBP-1 in plasma and dried blood extracts Paired plasma and dried blood extracts from fresh blood samples (n=40) were analyzed for IGFBP-1. Correlation of values in plasma fraction vs those measured in dried blood extract are shown. y=3.84+0.73x (r=0.948).

IGF-I and IGFBP-3 levels measured in plasma fractions and in the corresponding whole blood and dried blood filter paper extracts of freshly drawn samples (n=46) were compared. The plasma IGF-I and IGFBP-3 levels ranged from 36–575 ug/L, 0.87–5.9 mg/L and 6.4–52 arbitrary units/L, respectively. Regression analysis of data showed acceptable linear relationship between plasma values and those measured in whole blood and dried blood extracts (FIGS. 4–5). For these analytes, the blood spot values correlated well with the plasma levels (FIGS. 6–8).

TABLE 10

Hematocrit Effect on Measured IGF-I, and IGFBP-3 Concentrations in Whole Blood and Dried Blood Extract

| | Percent Change from Corresponding Original Sample Value[a] | | | |
|---|---|---|---|---|
| | IGF-I (ug/L) | | IGFBP-3 (mg/L) | |
| Hematocrit | WB[b] | Extract | WB | Extract |
| 0.70 | −60 | −26 | −72 | −38 |
| 0.62 | −43 | −27 | −49 | −17 |
| 0.434 | −15 | +6.1 | −18 | +2.2 |
| 0.33 | 0 | 0 | 0 | 0 |
| 0.27 | +2.5 | +2.8 | +11 | +14 |
| 0.20 | +23 | +4.8 | +24 | +6 |
| 0 (plasma) | +33 | −7.3 | +58 | +4 |

[a]Value of the 0.33 hematocrit specimen
[b]WB = Whole blood

EXAMPLE 7

Comparison of IGF-1 and IGFBP-3 in Plasma and Corresponding Dried Blood in Various Species This is a prophetic example. Whole blood samples from cows, pigs, goats and sheep is collected via venous draw from the jugular vein. Whole blood samples from rabbits are collected from the ear vein. Whole blood samples from rats are collected from heart puncture or tail clip. Whole blood samples from chicken are collected from heart puncture or wing vein. For guinea pigs, orbital whole blood samples are collected. Whole blood samples from fish are collected from tail fins or gills. The whole blood samples from the above species are either directly spotted on blood collection filter paper cards obtained from Schleicher and Schuell or are first collected in tubes containing anticoagulants, such as EDTA, and then applied to the blood collection filter paper cards. A portion of the whole blood from each of the above samples is allowed to stand at room temperature for 2 hours, centrifuged and supernatant plasma collected in separate tubes.

The dried blood spots are extracted as described in Examples 1, 2, and 3. The concentrations of IGF-I and IGFBP-3 are determined on the paired "blood spot" and "plasma" samples using the "analytical Procedure" described earlier. An excellent correlation is obtained between the "blood spot" and "plasma" samples, indicating the validity of the blood spot measurement of these analytes.

Many other variations and modifications may be made in the methods herein described, by those having experience in this art, without departing from the concept of the present invention. Accordingly, it should be clearly understood that the methods described in the foregoing description are illustrative only, and not intended as a limitation on the scope of the invention.

What is claimed is:

1. A method of determining concentrations of an insulin-like growth factor binding protein or acid labile subunit comprising the steps of:
    (a) collecting blood from a subject;
    (b) applying said blood to a solid support and drying said blood;
    (c) extracting said dried blood from said solid support with a buffer of about pH 7.0–8.5 to form a blood extract of about pH 7.0–8.5; and
    (d) testing said blood extract of about pH 7.0–8.5 for the concentration of insulin-like growth factor binding protein or acid labile subunit with an antibody directed against insulin-like growth factor binding protein or acid labile subunit.

2. The method according to claim 1 wherein said blood collecting step is conducted by capillary puncture.

3. The method according to claim 2 wherein said capillary puncture is selected from the group consisting of finger prick, thumb prick, or ear lobe prick.

4. The method according to claim 1 wherein said solid support is a paper medium.

5. The method according to claim 4 wherein said paper medium is filter paper.

6. The method according to claim 1 wherein said extracting step is conducted for a period of about thirty minutes to about two hours.

7. The method according to claim 1 wherein said extracting step is conducted for a period of about one hour.

8. The method according to claim 1 wherein said buffer extract comprises a buffer and protein.

9. The method according to claim 8 wherein said buffer comprises a buffer selected from the group consisting of Tris, borates, carbonates and phosphates.

10. The method according to claim 1 wherein said insulin-like growth factor binding protein is selected from the group consisting of insulin-like growth factor binding protein -1, -2, -3, -4, -5, and -6.

11. The method of claim 1, wherein said buffer extract consists essentially of an aqueous buffer, a detergent, optionally bovine serum albumin and optionally a salt.

12. The method of claim 11,
    wherein the aqueous buffer is selected from the group consisting of $dH_2O$, Tris, borates, acetates, and phosphates,
    wherein the detergent is selected from the group consisting of Tween 20 and sodium dodecyl sulfate, and
    wherein the salt is selected from the group consisting of NaCl, KCl, $MgCl_2$, and $CaCl_2$.

* * * * *

UNITED STATES PATENT AND TRADEMARK OFFICE
CERTIFICATE OF CORRECTION

PATENT NO.   : 6,066,464
DATED        : May 23, 2000
INVENTOR(S)  : Khosravi et al.

It is certified that error appears in the above-identified patent and that said Letters Patent is hereby corrected as shown below:

Drawings,
Replace FIGS. 6-8 with the attached FIGS. 6-8.

Signed and Sealed this

Tenth Day of September, 2002

Attest:

JAMES E. ROGAN
Attesting Officer          Director of the United States Patent and Trademark Office